United States Patent [19]

Bourgeois et al.

[11] Patent Number: 5,068,113
[45] Date of Patent: Nov. 26, 1991

[54] CHLOROFIBERS WITH PERMANENT ANTISEPTIC CHARACTER AND PROCESS FOR THEIR PRODUCTION

[75] Inventors: Michel Bourgeois, Lyons; Roger Chatelin; Daniel Wattiez, both of Lissieu Par Lozanne; Michel Sotton, St Cyr Au Mont d'Or; François Belet, Tronville en Barrois; Georges Achard, Decines, all of France

[73] Assignees: Institut Textile de France; Rhovyl, both of France

[21] Appl. No.: 409,809

[22] Filed: Sep. 20, 1989

[30] Foreign Application Priority Data

Sep. 27, 1988 [FR] France .................. 88 13059

[51] Int. Cl.$^5$ .................. A01N 25/34; A61K 9/14; A61K 33/28; C07F 3/12
[52] U.S. Cl. .................. 424/496; 424/402; 424/404; 424/405; 424/443; 424/486; 514/715; 514/717; 514/970; 556/121; 556/123; 556/126; 556/128; 556/7
[58] Field of Search .................. 424/78, 402, 404, 405, 424/443, 486, 496; 514/715, 717, 970; 556/121–123, 126, 128, 240, 336

[56] References Cited

U.S. PATENT DOCUMENTS 4,556,721 12/1985 Wattiez et al. .................. 514/496
4,931,577 6/1990 Bourgeois et al. .................. 556/123

FOREIGN PATENT DOCUMENTS 8300442 12/1982 France .

Primary Examiner—Thurman Page
Assistant Examiner—Carlos Azpuru
Attorney, Agent, or Firm—Ladas & Parry

[57] ABSTRACT

The fibrous polymeric material based on polyvinyl chloride contains at least one antiseptic mercury derivative distributed in its polymeric structure in the form of a substantially molecular and practically non-releasable dispersion.

The preferred mercury derivatives have the following general formula:

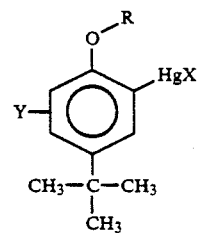

in which Y is H or HgX. If the concentration of the derivative is equal to at least 0.5% by weight, relative to the chlorofiber, the latter has a permanent antiseptic character.

This material is obtained by incorporating the above-mentioned derivative into the collodion when the chlorofiber is spun.

9 Claims, No Drawings

CHLOROFIBERS WITH PERMANENT ANTISEPTIC CHARACTER AND PROCESS FOR THEIR PRODUCTION

The present invention relates to a fibrous material based on polyvinyl chloride—designated hereafter by the general term "chlorofiber"—which has a permanent antiseptic character, even after several washes, without a significant reduction in the antiseptic character.

The use of certain mercurobutol derivatives for protecting textile substrates by giving them an antiseptic character has already been described, especially in French patent No. 8300442. These known derivatives contain, bonded to the phenol ring of the mercurobutol, a functional group which is capable of partaking in a polymerization or polyaddition reaction, for example an allyl, vinyl or acrylic group. The textile substrate is protected by reacting said derivative with the polymeric structure of the textile substrate in a polymerization or polyaddition reaction. This reaction is preferably a grafting reaction and uses a monomer. Thus the structure of the textile polymer contains grafts to which the mercurobutol derivatives are bonded.

This known technique has the disadvantage that a special treatment has to be carried out on the textile material. This treatment involves a complementary reactant in the case of grafting, with localization of the antiseptic derivative on the grafts.

A fibrous polymeric material, especially a textile material, has now been found which has a permanent antiseptic character without the stated disadvantage; it is this discovery which forms the subject of the invention. Said material is based on polyvinyl chloride. According to the invention, it contains at least one antiseptic mercury derivative distributed in its polymeric structure in the form of a substantially molecular and practically non-releasable dispersion, said derivative containing at least one benzene ring and comprising on the one hand a radical HgX, in which X is selected from F, Cl, Br, I, OH, CH$_3$COO, CN, SCN, NO$_3$ and OB-(OH)$_2$, and on the other hand, bonded to a benzene ring, at least one group —OR or —COOR, in which R is a functional group which is capable of partaking in a polymerization or polyaddition reaction.

Thus the antiseptic agent is distributed in the polymeric structure of the fibrous material in the form of a substantially molecular dispersion. This distribution is homogeneous throughout the bulk of the material. It is different in every respect from that which can be encountered in traditional inclusions, in which the inclusion product takes the form of aggregates of considerable size which are more or less well distributed in the bulk of the material.

Furthermore, contrary to what might have been expected of an antiseptic agent in the form of a substantially molecular dispersion, said agent is practically non-releasable, i.e. it remains in place in the polymeric structure, even after several washes. One may attempt to explain this permanency by the possible interactions between the polyvinyl chloride and the ethylenic bond of the functional group R.

The presence of mercury in the form of at least one HgX radical gives the derivative its antiseptic character. For example, in the case where the mercury derivative is a mercurobutol derivative, the antiseptic character is of the same order as that of mercurobutol.

Preferably, in the antiseptic mercury derivatives included in a fibrous material based on polyvinyl chloride in the form of a substantially molecular and practically non-releasable dispersion, the HgX radical is bonded to the benzene ring; also, said derivatives preferably comprise, bonded to the benzene ring, at least one alkyl group having a carbon number less than or equal to 5.

The preferred derivatives have the following general formula:

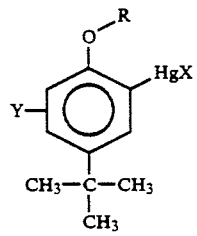

in which Y is H or HgX.

Among these, there may be mentioned 2-bromomercuri-4-tert-butylphenyl allyl ether, for which R is the allyl group (CH$_2$=CH—CH$_2$—) and Y is H, and 2-bromomercuri-4-tert-butylphenyl acrylate, for which R is the acrylic group (CH$_2$=CH—CO—) and Y is H.

The antiseptic mercury derivatives included in the fibrous material based on polyvinyl chloride can be in the form of a mixture, if desired; for example, it is possible to have both 2-bromomercuri-4-tert-butylphenyl allyl ether and 2-bromomercuri-6-chloromercuri-4-tert-butylphenyl allyl ether in proportions of 90/10 respectively.

The fibrous material based on polyvinyl chloride is in the form of fibers, filaments, woven fabrics, knitted fabrics, ready-made articles or nonwovens. Whatever form it is in, it retains antiseptic properties.

A further object of the invention is to protect a process for the manufacture of the above-mentioned fibrous polymeric material. This process is of the known type in which polyvinyl chloride is dissolved in a solvent based on carbon disulfide and acetone and then spun. According to the invention, at least one antiseptic mercury derivative is incorporated, before spinning, into the collodion consisting of the polyvinyl chloride dissolved in the solvent, said derivative containing at least one benzene ring and comprising on the one hand at least one radical HgX, in which X is selected from F, Cl, Br, I, OH, CH$_3$COO, CN, SCN, NO$_3$ and OB(OH)$_2$, and on the other hand, bonded to a benzene ring, at least one group —OR or —COOR, in which R is a functional group which is capable of partaking in a polymerization or polyaddition reaction. It has been noted that the above-mentioned mercury derivatives are themselves soluble in the solvent based on carbon disulfide and acetone which is used to prepare the collodion of polyvinyl chloride. By virtue of being dissolved in this way, said derivatives are distributed in the collodion in a homogeneous and substantially molecular manner, and they will preserve this distribution in the fibrous material after spinning.

Preferably, the mercury derivative is incorporated into the collodion by being dissolved in the solvent before the polyvinyl chloride is dissolved.

The invention and the advantages it provides will be understood more clearly on reading the following description of a complete Example of the preferred embodiment of the invention, which comprises the manufacture of the polymeric material, the definition of the structure of the material and the antiseptic properties of articles produced with said material.

The chosen mercury derivative is 2-bromomercuri-4-tert-butylphenyl allyl ether. The starting material for the preparation of this derivative is mercurobutol, a standard product, which is reacted with allyl bromide according to the following equation:

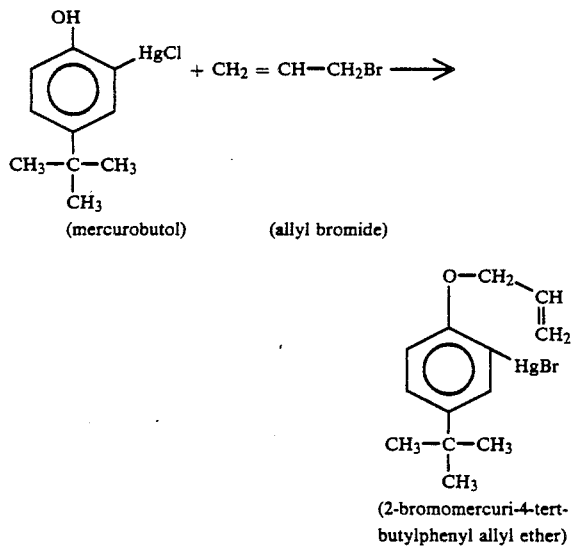

More precisely, 9.3 g of mercurobutol are taken and dissolved in 50 ml of hot denatured alcohol. 2 g of potassium hydroxide are added cautiously. A thick white precipitate forms. 4.4 ml of allyl bromide are added to 21 ml of denatured alcohol and this is mixed with the precipitate, which becomes more fluid. The mixture is heated for two hours at the boiling point of the alcohol and is then filtered hot to give 9.43 g of 2-bromomercuri-4-tert-butylphenyl allyl ether with a yield of 92%. This product is pure, as could be verified by thin layer chromatography. It melts at 100° C. and is in the form of a water-insoluble white powder.

This product, which will be denoted by the term "derivative" in the remainder of the present description, is added to a mixture of carbon disulfide and acetone—the usual solvent for polyvinyl chloride in the spinning of chlorofibers—into which various stabilizers have been incorporated. The solution obtained is placed in a cooling medium at −18° C. After cooling, the polyvinyl chloride polymer, which is also at −18° C., is incorporated in powder form. After stirring, the mixture is poured into the plunger cylinder of the spinning installation. As the temperature rises slowly to 25° C., the viscosity of the mixture increases to values of the order of 2000 Pl. It is this viscous mixture which constitutes the collodion, i.e. the base material for spinning.

The collodion is compressed in the plunger cylinder and passes through a first heat exchanger at 120° C., a second heat exchanger at 75° C. and then a filtration system whose purpose is to remove the impurities, any bubbles present and the insoluble materials, and also to even out the flow rate and the speed of the collodion before it enters the spinneret.

The spinneret used in the present case is an 80-strand 60-micrometer spinneret. The spinning speed is 180 m/min. On leaving the spinneret, the filament undergoes slight stretching in a ratio of 1.1 in the recovery cell; it is recovered in a rotating pot after it has been appropriately sized by means of a lick roller. It is then taken up for stretching and setting in the manner which is conventional in chlorofiber spinning.

The fibrous material obtained, based on polyvinyl chloride, contains the derivative distributed in its polymeric structure in the form of a substantially molecular and practically non-releasable dispersion.

The derivative is followed through the various stages of the manufacturing process and in the resulting chlorofiber by colorimetric determination of the mercury with dithizone after mineralization of the fibers in an acidic and oxidizing medium (sulfuric acid and potassium permanganate). For concentrations of derivatives of the order of 1 to 2 parts per thousand, relative to the polyvinyl chloride, no loss of the derivative has been observed, all the derivative introduced into the solvent being found in the chlorofiber.

Several extractions are carried out on the chlorofiber with methanol, which is a solvent for the derivative, and no significant modification of the amount of derivative in the fibrous polymer is observed; the same applies to ready-made articles produced with the chlorofiber after they have been washed several times in a domestic washing machine. In view of the precision of the measurements made by current methods, it can be said that the derivative is practically non-releasable from the material.

Furthermore, microscopic analysis of the chlorofiber does not make it possible to detect the presence of the derivative in the polymeric structure, even at a magnification of ×100,000 by scanning electron microscopy (SEM) or by transmission electron microscopy (TEM). Thus the derivative is in the form not of aggregates which are visible by microscopic analysis, but of a substantially molecular dispersion throughout the polymeric structure of the material.

EXAMPLE 1

To prove the antiseptic protection provided by the derivative in the polymeric structure of the chlorofiber, tests were carried out in a gelose medium with *Escherichia coli* 7624 IP, 25922 ATCC as the bacterial strain. The gelose medium is a Mueller Hinton medium, reference 51 861 Bio Mérieux, containing the following components in g/l of distilled water at pH 7.4:
Beef infusion: 300
Bio Case: 17.5
Starch: 1.5
Gelose: 17.
The gelose medium is deposited in a Petri dish to a uniform thickness of 4 mm and then inoculated with a suspension of germs, namely 0.1 ml of a suspension containing $10^5$ germs/ml.

Chlorofibers having different concentrations of derivative were produced. These concentrations are given in mg of mercury/g of chlorofiber:
Experiment 1: 4.76 mg of Hg
Experiment 2: 0.95 mg of Hg
Experiment 3: 0.47 mg of Hg.

After spinning and extraction with methanol, the chlorofibers were knitted and washed. For each experiment, pieces of knitted fabric were deposited on the gelose in Petri dishes. After heating in an oven for 24 h at 35.5° C., the preparation was observed under a stereoscopic microscope. In all cases, irrespective of the concentration of derivative in the chlorofiber, it was observed that the bacterial colonies had developed normally at the periphery of the knitted fabric, but that the knitted fabric itself was bacteriologically clean, not being the seat of any incipient development and even less of bacterial proliferation, in contrast to what could be observed on a control knitted fabric produced from chlorofiber not containing derivative.

EXAMPLE 2

The purpose of this series of experiments was to find approximately the minimum concentration of derivative which resulted in effective protection of the chlorofiber. The concentrations were as follows:
Experiment 4: 0.465 mg of mercury/g of chlorofiber
Experiment 5: 0.24 mg of mercury/g of chlorofiber
Experiment 6: 0 mg of mercury/g of chlorofiber (control).

The tests on gelose were performed with a bacterial strain which produces colored colonies, namely *Staphylococcus aureus* (ATCC 9 144), which is orange for large colonies. The inoculum is more concentrated at $10^6$ germs/ml. The results obtained in Experiment 4 confirm those of the previous Example; the knitted fabric is white and clean; all the bacterial colonies remain outside the fibrous mass: there is no inhibition zone around the fibers or around the knitted fabric, so there is no release of the derivative.

By contrast, as far as the control (Experiment 6) is concerned, a considerable bacterial development is observed in the fibers containing the culture medium. This development results in a yellow coloration in the mass of the knitted fabric, which is yellow and dirty.

As far as Experiment 5 is concerned, the result is similar to that of Experiment 6; the knitted fabric is yellow and dirty although the yellow color is less intense. At this concentration in the chlorofiber, the derivative does not seem to provide the article with effective antiseptic protection. The antiseptic character of the article made of chlorofiber according to the invention is assured for a concentration of derivative of at least 0.5%, which corresponds to about 0.25 mg of mercury/g of chlorofiber.

The invention is not limited to the product and the embodiment described above by way of example. It encompasses all the variants thereof. In particular, the included antiseptic mercury derivative can be obtained from known antiseptic mercury products other than mercurobutol, for example mercurophen, mercurosal or mercurochrome. All these products contain in their formula at least one benzene ring, at least one radical HgX, in which X is OH, and, bonded to the benzene ring, at least one group OR' or COOR'. Thus an antiseptic mercury derivative will easily be obtained by reacting an allyl halide with one of the mercury products mentioned above; in this case the group —OR will be the group —O—$CH_2$—CH=$CH_2$.

What is claimed is:

1. A fibrous polymeric material based on polyvinyl chloride which contains at least one antiseptic mercury derivative distributed in its polymeric structure in the form of a substantially molecular and practically non-releasable dispersion, said derivative being present in a concentration of at least 0.25 mg of mercury/g of chlorofiber and containing at least one benzene ring and comprising on the one hand at least one radical HgX, in which X is selected from F, Cl, Br, I, OH, $CH_3COO$, CN, SCN, $NO_3$ and $OB(OH)_2$, and on the other hand, bonded to a benzene ring, at least one group —OR or —COOR, in which R is a functional group which is capable of partaking in a polymerization or polyaddition reaction, said derivative being not fixed on the polymeric structure of the material by a reaction of polymerization or of polyaddition, but being distributed on its polymeric structure in the form of a molecular and practically non-releasable dispersion.

2. A material according to claim 1, wherein R is an allyl, vinyl or acrylic group.

3. A material according to claim 1, wherein the group —HgX of the mercury derivative is bonded to the benzene ring.

4. A material according to claim 1, wherein the derivative contains, bonded to the benzene ring, an alkyl group having a carbon number less than or equal to 5.

5. A material according to claim 4, wherein the mercury derivative has the general formula

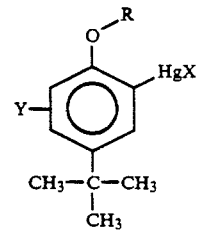

in which Y is H or HgX.

6. A material according to claim 5 which contains, distributed in its structure, two mercury derivatives both having the formula

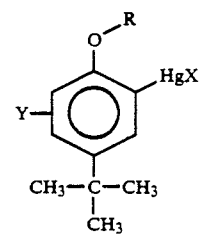

for which Y is H in the first derivative and Y is HgX in the second derivative.

7. A material according to claim 5, wherein the mercury derivative is at a concentration of at least 0.5% by weight, relative to the chlorofiber, in order for it to have permanent antiseptic properties similar to those of mercurobutol.

8. A process for the manufacture of the fibrous polymeric material according to claim 1, of the type in which the polyvinyl chloride is dissolved in a solvent based on carbon disulfide and acetone and then spun, which process consists in incorporating at least one antiseptic mercury derivative into the collodion consisting of the polyvinyl chloride dissolved in the solvent, said derivative containing at least one benzene ring and comprising on the one hand at least one radical HgX, in which X is selected from F, Cl, Br, I, OH, $CH_3COO$, CN, SCN, $NO_3$ and $OB(OH)_2$, and on the other hand, bonded to a benzene ring, at least one group —OR or —COOR, in which R is a functional group which is capable of partaking in a polymerization or polyaddition reaction.

9. A process according to claim 8 which consists in dissolving the mercury derivative in the solvent before the polyvinyl chloride is dissolved.

* * * * *